United States Patent [19]
Robison

[11] Patent Number: 4,885,275
[45] Date of Patent: Dec. 5, 1989

[54] VANCOMYCIN-HCL SOLUTIONS AND THE LYOPHILIZATION THEREOF

[75] Inventor: Robert L. Robison, Greenwood, Ind.

[73] Assignee: Eli Lilly and Company, Indianapolis, Ind.

[21] Appl. No.: 109,885

[22] Filed: Oct. 15, 1987

[51] Int. Cl.$^4$ ............ A61K 37/02; C07K 7/64; C07K 9/00
[52] U.S. Cl. .................... 514/8; 424/115; 424/118; 530/317; 530/322; 536/16.9; 536/18.5; 540/355
[58] Field of Search .............. 514/8; 424/115, 118; 540/355; 536/16.9, 18.5; 530/317

[56] References Cited
U.S. PATENT DOCUMENTS

| | | | |
|---|---|---|---|
| 3,067,099 | 12/1962 | McCormick et al. | 167/65 |
| 4,228,160 | 10/1980 | Szejtli | 536/103 |
| 4,378,348 | 3/1983 | Nishida | 424/118 |
| 4,497,803 | 2/1985 | Harada | 514/450 |
| 4,547,488 | 10/1985 | Merkel | 514/10 |

Primary Examiner—Howard E. Schain
Assistant Examiner—Choon P. Koh
Attorney, Agent, or Firm—William B. Scanlon; Leroy Whitaker

[57] ABSTRACT

Gel-free concentrated aqueous formulations of vancomycin hydrochloride are provided which comprise the antibiotic salt at a concentration between about 12% and about 50% w/v and a gel-inhibiting compound, e.g., ethanol, at a concentration between about 1% and about 20% v/v. The gel-free formulations are especially useful in a freeze-drying process for preparing vancomycin hydrochloride as a dry flowable powder in bulk or in unit-dosage form.

13 Claims, No Drawings

VANCOMYCIN-HCL SOLUTIONS AND THE LYOPHILIZATION THEREOF

BACKGROUND OF THE INVENTION

This invention relates to concentrated aqueous solutions of the antibiotic vancomycin hydrochloride and to a process for the lyophilization thereof.

Vancomycin is described in U.S. Pat. No. 3,067,099. It is a well known antibiotic often prescribed for the treatment of staphylococcal infections, particularly infections caused by methicillin-resistant strains of staphylococcus. Vancomycin is isolated from the fermentation broth in which it is produced. It is formulated for pharmaceutical use as the hydrochloride salt, vancomycin hydrochloride.

Vancomycin hydrochloride is supplied for oral and parenteral use as a dry solid in sterile vials or small bottles. The dry solid form of vancomycin hydrochloride is obtained by lyophilization of aqueous solutions of the hydrochloride. The vancomycin hydrochloride solutions are prepared for lyophilization by treating vancomycin free base in water with hydrochloric acid.

Manufacturing scale lyophilizations are desirably carried out using as small a volume as possible to reduce lyophilization time. In a typical lyophilization technique, an aqueous solution of the active ingredient is lyophilized directly in the container in which it is to be supplied, for example sterile vials or pharmacy bottles. Accordingly, the ability to obtain the desired concentration of the active ingredient in the aqueous solution to be lyophilized is highly important, since one requires the desired weight of active ingredient in the end use container.

The solubility of vancomycin hydrochloride in water at room temperature is about 200 mg/ml. However, solutions containing vancomycin hydrochloride at a concentration of about 11 to about 12%, weight/volume, and higher have a high tendency to form gels. This gel formation results in severe handling problems. Further, when lyophilization is complete the vancomycin hydrochloride is obtained in the form of a dry plug which may dissolve slowly rather than as an easily soluble, flowable powder.

The gel formation appears to be a reversible process. Gel solutions can be restored to their original viscosity by pH adjustment. These aqueous gels apparently result from molecular associations which form non-covalently bonded polymeric structures.

This invention provides stable, gel-free concentrated aqueous solutions of vancomycin hydrochloride and a process for preparing vancomycin hydrochloride as a dry soluble, free-flowing powder from the concentrated solutions.

SUMMARY OF THE INVENTION

This invention provides concentrated aqueous solutions of vancomycin hydrochloride stable to gel formation which comprise between about 12% and about 50% w/v of vancomycin hydrochloride and between about 1% and about 20% v/v of a gel-inhibiting compound selected from among an alcohol of the group ethanol, n-propanol, iso-propanol or propylene glycol, an ester of the group isopropyl acetate or n-propyl acetate and a ketone of the group acetone or methyl ethyl ketone.

The formulations provided by the invention are especially useful in a freeze-drying process for providing vancomycin hydrochloride in a readily soluble solid form ready for dissolution and administration. The formulations allow one to obtain aqueous solutions of vancomycin hydrochloride which are gel-free and which can be freeze-dried in much shorter time than corresponding concentrated gel-containing solutions.

DETAILED DESCRIPTION OF THE INVENTION

The aqueous vancomycin hydrochloride formulations of this invention comprise between about 12% and about 50% w/v of vancomycin hydrochlorlde and between about 1% and about 20% v/v of a compound selected from among an alcohol of the group ethanol, n-propanol, isopropanol or propylene glycol, an ester of the qroup n-isopropyl acetate or isopropyl acetate and a ketone of the group acetone or methyl ethyl ketone.

The vancomycin hydrochloride formulations are prepared by mixing water and the alcohol, ester or ketone, in an amount calculated to provide the desired final concentration, with vancomycin-free base. The slurry of the free base is treated with hydrochloric acid in an amount sufficient to convert the free base to the hydrochloride salt and to adjust the pH to about 3.1 to about 3.3. Water is then added to the desired volume and the formulation is mixed thoroughly. In preparing the formulations, desirably the amount of the alcohol, ester or ketone needed to achieve between about 1% and about 20% of the final volume is used in forming the aqueous slurry of the free base. Likewise, the amount of vancomycin-free base used to make up the initial slurry is that needed to acquire the desired concentrations of vancomycin hydrochloride of the final formulation. The concentration of hydrochloric acid used to form the salt is conveniently about 20%, although somewhat more dilute, or concentrated acid may be used.

In an example of the preparation of a preferred formulation, 10 g-size vial, comprising ethyl alcohol, 35 ml of water and 5 ml of 95% ethyl alcohol USP are mixed and 10 g of vancomycin-free base are added to form a slurry. Hydrochloric acid (15%) is added to the slurry with stirring until the pH is adjusted to about 3.1 to 3.3. Water is then added to a total volume of 50 ml, having a 20% concentration.

The formulations of this invention are useful as concentrated solutions of vancomycin hydrochloride especially suitable for freeze drying to provide a free-flowing vancomycin hydrochloride powder for parenteral administration. Solutions of vancomycin hydrochloride in water at concentrations above about 12% w/v form gels, particularly when agitated by stirring, shaking or blending. The nature of the gel and the cause of its formation has not been determined. Thus, when processing an aqueous solution of vancomycin.HCl at a concentration higher than about 12%, the filtration was poor and time-consuming as is the filtration of most solutions containing gels. Further, the lyophilization of such partially or completely gelled solutions requires substantially longer times and results in a poorly soluble dried plug of the antibiotic rather than a readily soluble flowable dry powder as desired.

The formulations of this invention comprise a gel-inhibiting amount of ethyl alcohol, n-propyl alcohol, isopropyl alcohol, propylene glycol, n-propyl acetate, isopropyl acetate, acetone or methyl ethyl ketone. These gel-inhibiting compounds were determined in a series of experiments carried out with a variety of compounds, most of which are pharmaceutically acceptable. The experiments were carried out to determine the effect on gel formation in aqueous solutions of vancomycin HCl at a concentration of 20% w/v. The solutions were prepared as follows. An aqueous vehicle containing the test compound in an amount sufficient to provide 10% v/v in the final solution was prepared with water. Vancomycin-free base was added to the aqueous vehicle in an amount sufficient to provide a 20% w/v concentration in the final solution. The slurry of base in the aqueous vehicle was treated with 20% hydrochloric acid to form vancomycin.HCl salt and to adjust the pH to about 3.2. The solution which formed was kept covered to avoid loss of the test compound and water was added to the final volume. The solution was blended in a Waring blender at high speed for 3 minutes and then transferred to clear bottles to observe for gel formation. The results of the experiments are listed below in Table 1.

TABLE 1

Gel Inhibition in Concentrated Aqueous Vancomycin.HCl Solutions

| Test Compound | Test Result* |
|---|---|
| Methanol | G |
| Ethanol | NG |
| Isopropanol | NG |
| Acetone | NG |
| Methyl ethyl ketone | NG |
| Ethyl acetate | G |
| Isopropyl acetate | NG |
| Propylene glycol | NG |
| Glycerin | G |
| Control** | G |

*G = gel formation
NG = No gel formation
**Vancomycin.HCl in water at a concentration of 20% w/v The results shown in Table 1 shed little light on the gel formation or the inhibition thereof since such closely related compounds as methanol and ethanol behave differently.

The solubility of vancomycin.HCl in some of the gel inhibitory compounds was determined as follows. A two-gram quantity of chromatographically purified vancomycin hydrochloride was added to 100 ml of each compound under consideration. Fresh compound was used when possible to minimize the water content. It was anticipated that most solubilities would fall well below the 20 mg/ml level. The mixtures were stirred at a moderate rate for 4 hours, with sample aliquots removed at timepoints of 10 minutes, 2 hours and 4 hours. The mixtures were then allowed to stand overnight. A final aliquot was taken at the 20- to 24-hour timepoint. The sample aliquots were assayed by UV absorption measurements or HPLC with UV detection.

UV absorption at 280 nm was used to measure the concentration of vancomycin in the sample solutions made with the transparent solvents. Each sample was filtered through medium-pore filter paper and diluted with water to provide an absorption less than 1.0 A. The remaining compounds, acetone and ethyl acetate, required solvent removal before the measurement step. After filtration, sample aliquots were dried under nitrogen and reconstituted with an aqueous buffer for assay by HPLC. The propylene glycol sample were also assayed by HPLC after appropriate dilution without a drying step.

The results from this study are shown in Table 2. A wide range of solubilities are observed for these compounds, with gel formation observed in ethanol and propylene glycol.

TABLE 2

Vancomycin.HCl Solubility in Gel Inhibitory Compounds

1. UV Assays

| | Solubility (mg/ml) | | | |
|---|---|---|---|---|
| Compound | 10 min | 2 hrs | 4 hrs | 20 hrs |
| Methanol | 5.3 | 3.7 | 3.1 | 2.4 |
| Ethanol, absolute | 0.7 | 2.0 | ° | ° |
| Isopropanol | 0.04 | 0.04 | 0.10 | 0.07 |

2. HPLC Assays

| Compound | 10 min | 2 hrs | 4 hrs | 20 hrs |
|---|---|---|---|---|
| Propylene glycol | 3.0 | ° | ° | * |
| Ethyl acetate | <0.01 | <0.01 | <0.01 | <0.01 |
| Acetone | <0.01 | <0.01 | <0.01 | <0.01 |

*Gel formation

The results in Table 2 show that gel formation occurs in non-aqueous media as well. In particular, it is noted that with the preferred gel inhibitory compound of the invention, ethyl alcohol, vancomycin.HCl also forms gel at concentrations at about 2 mg/ml.

As was mentioned above, the vancomycin.HCl formulations of this invention are especially suited for preparing, via freeze drying, vancomycin.HCl as a flowable powder for reconstitution prior to administration. Because gel formation is inhibited, aqueous solutions of vancomycin.HCl at higher concentrations can be freeze-dried in shorter drying times than less concentrated solutions. The formulations provided herein also allow greater flexibility in preparing a desired bulk size of the antibiotic in a smaller vial or bottle because of the lower volume of the concentrated gel-free formulations. For example, a 10 g bulk pharmacy vial can be conveniently and economically prepared directly in a 100-ml vial by freeze drying a 50 ml gel-free formulation containing vancomycin.HCl under sterile conditions at a concentration of 20% w/v. Further, the freeze-dried vancomycin.HCl is obtained as a flowable powder which is much more readily dissolved in a physiologically compatible fluid for administration than is the dried plug of the antibiotic salt obtained upon freeze drying of gelled or partially gelled solutions.

In a further aspect of this invention, there is provided a process for preparing vancomycin.HCl as a dry flowable powder which comprises (a) freezing to a temperature below about −30° C. a gel-free aqueous formulation comprising vancomycin.HCl at a concentration of between about 12% and about 50% w/v and between about 1% and about 20% v/v of a gel inhibitor compound selected from among an alcohol of the group ethanol, n-propanol, isopropanol or propylene glycol, an ester of the group n-propyl acetate or isopropyl acetate, and a ketone of the group acetone or methyl ethyl ketone; (b) applying a vacuum to said frozen gel-free formulation to a reduced pressure of between about 50 microns and about 300 microns and (c) slowly heating said frozen gel-free formulation to a final temperature of between about 25° C. and about 40° C.

The freeze drying of a formulation of the invention is carried out in conventional freeze-drying equipment. Preferably, the process is carried out in the container to be used for the final formulation. Preferably, ethanol is the gel inhibitory compound and is present at a concentration of about 10% by volume. The concentration of vancomycin.HCl in the gel-free formulation is preferably above 10% w/v, e.g., between about 10% and about 30% w/v.

The vacuum applied in the process is variable; however, best drying conditions generally occur at pressures of between about 100 microns and about 200 microns. Once the pressure is reduced, the frozen formulation is gradually heated to a final temperature between about 25° C. and about 40° C. and, preferably, at about 30° C. to about 35° C. The heat is applied gradually to prevent untoward loss of antibiotic due to fly-off of dried particles as moisture and vapor is escaping from the drying mass.

The process of the invention can be used to prepare vancomycin.HCl in bulk or in unit-dosage formulations. For example, 10 g bulk pharmacy vials or bottles can be prepared in the process as described hereinabove with a 50 ml gel-free formulation containing vancomycin.HCl at a concentration of 20% w/v in a 100-ml vial. Unit-dosage formulations for parenteral use may be obtained in the process by drying a gel-free formulation at the appropriate concentrations in the desired size vial or bottle. Such unit-dosage formulations typically contain 0.5 g or 1 g of dry flowable vancomycin.HCl per vial.

In yet a further aspect of this invention, there are provided aqueous formulations of vancomycin hydrochloride which prevent gel formation during the freeze-drying process. Increased concentrations of vancomycin hydrochloride which occur during the freezing process, irrespective of the concentrations in the starting solution, can result in gel formation. The resulting dry solid obtained possesses a poor dissolution rate. The invention provides aqueous formulations comprising less than about 12% w/v of vancomycin hydrochloride and between about 1% and about 20% v/v of a compound selected from the group consisting of ethyl alcohol, n-propanol, iso-propanol, propylene glycol, isopropyl acetate, n-propyl acetate, acetone and methyl ethyl ketone. According to this aspect of the invention, the formulations described above inhibit gel formation during freeze-drying and thus provide vancomycin hydrochloride in a readily soluble dry solid form.

The following example further illustrates the invention and is not intended to be limiting thereof.

EXAMPLE 1

Preparation of 10 g bulk pharmacy vial—lyophilized vancomycin.HCl

Vancomycin-free base (10 g) is added to a mixture of 35 ml of water and 5 ml of 95% ethyl alcohol USP to form a slurry. Hydrochloric acid (20%) is added dropwise to the slurry until the pH is adjusted to 3.1 and all of the base is converted to the hydrochloride salt. Water is then added to a final volume of 50 ml and the solution is filtered. The solution is transferred into a 100 ml vial and the solution lyophilized under the following conditions. The solution is frozen to a temperature below about −30° C., evacuated under vacuum to a pressure of about 150 microns and slowly warmed to 35° C. until dry. There are obtained about 10 g of vancomycin.HCl as a dry flowable powder.

I claim:

1. An aqueous gel-free formulation of vancomycin hydrochloride comprising between about 12% and about 50% w/v of vancomycin hydrochloride and between about 1% and about 20% v/v of a gel-inhibiting compound selected from among an alcohol of the group ethanol, n-propanol, isopropanol or propylene glycol, an ester of the group n-isopropyl acetate or isopropyl acetate and a ketone of the group acetone or methyl ethyl ketone.

2. The formulation of claim 1 comprising between about 1% and about 10% v:v of an alcohol.

3. The formulation of claim 2 wherein the alcohol is ethyl alcohol.

4. The formulation of claim 3 wherein the concentration of the ethyl alcohol is about 10% by volume.

5. The formulation of claim 1 comprising vancomycin hydrochloride at a concentration between about 12% w/v and about 30% w/v and ethyl alcohol at a concentration of about 5% and about 10% v/v.

6. The formulation of claim 1 wherein the gel-inhibiting compound is acetone or methyl ethyl ketone.

7. The formulation of claim 1 wherein the gel-inhibiting compound is propylene glycol.

8. The process for preparing vancomycin hydrochloride as a dry, readily soluble, solid which comprises (a) freezing to a temperature below about −30° C. a gel-free aqueous formulation of claim 1, (b) applying a vacuum to said frozen formulation to a reduced pressure between about 50 microns and about 300 microns and (c) slowly heating said frozen formulation to a temperature between about 25° C. and about 40° C.

9. The process of claim 8 where in the gel-free formulation comprises a gel inhibiting alcohol.

10. The process of claim 8 wherein the gel-free formulation contains vancomycin hydrochloride at a concentration of between about 20% w/v and about 30% w/v.

11. The process of claim 10 where in the gel-free formulation contains an alcohol as the gel-inhibiting compound.

12. The process of claim 11 wherein the alcohol is ethanol or propylene glycol.

13. The process of claim 11 wherein the alcohol is ethanol at a concentration of about 10% by volume.

* * * * *